United States Patent [19]

Dazey et al.

[11] Patent Number: 5,344,918

[45] Date of Patent: Sep. 6, 1994

[54] PROCESS FOR THE MANUFACTURE OF A HIGH-PURITY ACTIVATED FACTOR VII CONCENTRATE ESSENTIALLY FREE OF VITAMIN K-DEPENDENT FACTORS AND FACTORS VIIIC AND VIIICAG

[75] Inventors: Bernard Dazey; Mohamed Hamsany; Sylvia Enfedaque-Morer, all of Bordeaux, France

[73] Assignee: Association d'Aquitaine Pour le Developpement de la Transfusion Sanguine et des Recherches Hematologiques, Bordeaux, France

[21] Appl. No.: 988,776

[22] Filed: Dec. 10, 1992

[30] Foreign Application Priority Data

Dec. 16, 1991 [FR] France ................... 91 15601

[51] Int. Cl.$^5$ ............... A61K 35/16; A61K 35/14; A61K 39/00
[52] U.S. Cl. ..................... 530/381; 530/415; 530/416; 530/384
[58] Field of Search ............... 530/381, 415, 416, 384

[56] References Cited

U.S. PATENT DOCUMENTS

| | | | |
|---|---|---|---|
| 4,470,969 | 9/1984 | Pancham et al. | 530/384 |
| 4,473,553 | 9/1984 | Zuffi et al. | 530/381 |
| 4,540,473 | 9/1985 | Neurath et al. | 530/381 |

FOREIGN PATENT DOCUMENTS

WO89/12097 12/1989 PCT Int'l Appl. .

OTHER PUBLICATIONS

"Research Disclosure", vol. 269, Sep. 1986, Havant GB, pp. 564–565, S. Bjoern et al.

Primary Examiner—Howard E. Schain
Assistant Examiner—C. Lynn Touzeau
Attorney, Agent, or Firm—Dennison, Meserole, Pollack & Scheiner

[57] ABSTRACT

The invention relates to a process for the manufacture of a high-purity activated factor VII concentrate.

This process comprises the use of a plasma free of cryoprecipitate, preferably of human origin, as well as at least one purification step involving chromatography at least once on an ion exchange resin, and a factor VII activation step, wherein the first stage is direct activation of the factor VII in the crude supernatant of plasma free of cryoprecipitate, without the addition of exogenous proteins.

By virtue of the invention, the high-purity activated factor VII is essentially free of vitamin K-dependent factors and factors VIIIC and VIIICAg and has a factor VIIa/factor VII ratio greater than 5 with a specific activity of the activated factor VII greater than 200 IU/mg of proteins.

23 Claims, No Drawings

PROCESS FOR THE MANUFACTURE OF A HIGH-PURITY ACTIVATED FACTOR VII CONCENTRATE ESSENTIALLY FREE OF VITAMIN K-DEPENDENT FACTORS AND FACTORS VIIIC AND VIIICAG

The present invention relates essentially to the process for the manufacture of a high-purity activated factor VII concentrate essentially free of vitamin K-dependent factors and factors VIIIC and VIIICAg, and to the product obtained by this process.

The clotting factor responsible for reestablishing hemostasis in hemophiliacs who have circulating antibodies is known to be activated factor VII. This is present in the composition of activated prothrombin concentrates such as, for example, FEIBA ® or AUTOPLEX ®.

Various documents, such as WO-A-89/12097, WO-A-83/00016, EP-A-0 225 160, U.S. Pat. No. 4,637,932 and FR-A-2 622 108, have demonstrated the effective role of factor VIIa. In particular, the document EP-B1-0 225 160 demonstrates the efficacy of factor VIIa in reestablishing normal hemostasis in the case of hemorrhagic disorders not caused by factor VIII deficiencies or by inhibitors.

These and other documents describe different techniques for the purification of factor VII and factor VIIa. However, the techniques used are very complex, require numerous steps and are difficult to apply on the industrial and medical scale, or involve a high cost.

In U.S. Pat. No. 4,637,932, for example, PANCHAM describes a process for the purification of factors VII and factors VIIa from an aqueous solution containing plasma proteins, wherein these proteins are adsorbed on to a gel carrying divalent metal salts with an affinity for proteins binding to calcium, such as tricalcium phosphate in the form of hydroxyapatite from Biorad ®, and then desorbed with the aid of a buffer containing salts capable of displacing the bound proteins.

A complementary purification is then carried out with the aid of ion exchange chromatography of the DEAE type (DiEthylAminoEthyl), commercially available for example under the tradename DEAE-Sephadex ®, according to the procedure described in U.S. Pat. No. 3,717,708.

The document RESEARCH DISCLOSURE vol. 269, September 1986, HAVANT GB, pages 564–565, contains an article by BJOERN relating to the activation of clotting factor VII to factor VIIa. The method described consists in carrying out selective adsorption of the factor VII, on an ion exchange column of the DEAE-SEPHADEX, QAE-SEPHADEX or Mono Q type from PHARMACIA, in order to activate it. It should be noted that this method only appears to work when starting from a factor VII which has been previously purified by conventional techniques or obtained by genetic engineering methods, as stated on page 564.

By contrast, in the framework of the invention, it is sought to activate unpurified factor VII present in plasma.

The document EP-A-0 346 241=WO-A-89/12097=FR-A-2 632 524 to the Fondation Nationale de Transfusion Sanguine, or FNTS, describes a process for the preparation of a fraction rich in factor VIIa using a step for the calcium binding of a preeluate of PPSB after the addition of a kallikrein inhibitor such as aprotinin, which introduces a foreign protein capable of causing contamination. The first activation step is carried out with tricalcium phosphate, for which factor VII has a high affinity, after which desorption steps are carried out with salts capable of reseparating the proteins bound to the calcium, such as monosodium or disodium phosphate, and the activation of the factor VII is completed by activation with kaolin or Célite. Before viral inactivation, antithrombin III is added to prevent any premature precipitation (column 5, Example 2, lines 31 to 36). Finally, viral inactivation is carried out, after which the inactivating agents are removed by chromatography on a column of Q Sepharose. Albumin is finally added to stabilize the proteins (Example 2, column 5, lines 45–47). Thus this process is complicated and, in the course of the procedure, it is necessary to verify the activation and also to add three foreign proteins, namely aprotinin, antithrombin III and albumin, which can carry a potential risk of contamination. Finally, the factor VII obtained still contains appreciable amounts of other clotting factors, as shown by the Table in column 6, especially factor II, factor IX and factor X, which demonstrates the thrombogenic risk.

The document U.S. Pat. No. 4,473,553 to ZUFFI speaks first of all of a fraction known as the Cohn fraction, which results from the salting-out of the initial plasma one or more times with alcohol. This Cohn fraction is then treated with a mixture containing a very large proportion of calcium chloride with a small amount of a polyanionic adsorbent, which can be dextran sulfate (Example 1) or heparin (Example 2), for removing the lipoproteins by precipitation. In this mixture, the dextran sulfate has no detectable activating effect. The activation of the factor VII takes place at a later stage with hydroxyapatite.

The invention differs from said document by using the plasma directly; it is directly activated only by beads of dextran sulfate without lipoprotein precipitation at this stage, which subsequently simplifies the process and affords a very good degree of activation.

Furthermore, MICHALSKY et al. in FR-A-2 622 108 describe a process for the purification of factor VII by adsorption chromatography on DEAE-SEPHAROSE ®, followed by elution with a buffer solution containing 0.18–0.20M NaCl, which gives a factor VII having a specific activity of between 0.8 and 1, representing a very low degree of purification.

Finally, the article by HEDNER and KIESEL in J. Clin. (1983), 71, p. 1836–1841, describes the use of human activated factor VII in the treatment of two patients suffering from hemophilia A with a high proportion of inhibitors. The activated factor VII used by these authors in their treatment is a factor VII which has been purified by ion exchange chromatography (see p. 1837, left column) with the aid of a DEAE-Sepharose ® column using buffer solutions containing calcium chloride as the eluent. The factor VII is activated by using activated factor XII, itself obtained by activation with human kallikrein in the presence of dextran sulfate. This procedure is also complex and requires the addition of exogenous proteins, including activated factor XII and kallikrein, which have to be removed at the end of the purification step in order to obtain an activated factor VII of very high purity.

The main object of the present invention is therefore to solve the novel technical problem which consists in providing a solution making it possible to manufacture high-purity activated factor VII essentially free of vitamin K-dependent factors and factors VIIIC and VIIICAg.

A further object of the present invention is to solve this novel technical problem by means of a solution which does not involve the use of exogenous proteins to activate the factor VII.

Yet another object of the present invention is to solve the above-mentioned novel technical problem with a simple solution, especially in the factor VII activation step and also in the actual purification steps.

The present invention solves the above-mentioned technical problem for the first time in a simple and relatively inexpensive manner which can be used on the industrial and medical scale and which produces a high-purity activated factor VII essentially free of vitamin K-dependent factors and factors VIIIC and VIIICAg.

Thus, according to a first feature, the present invention provides a process for the manufacture of a high-purity activated factor VII concentrate, comprising the use of plasma free of cryoprecipitate, preferably of human origin, as well as at least one purification step involving chromatography at least once on an anion exchange resin, and a factor VII activation step, wherein the first stage is direct activation of the factor VII in the plasma free of cryoprecipitate, without the addition of exogenous proteins.

The activation of the factor VII is preferably carried out according to the invention by using dextran sulfate in pulverulent form, which is insoluble in said plasma. The dextran sulfate is preferably used in the form of beads. The size of the beads is not critical and commercially available dextran sulfate beads, such as the beads marketed by Sigma, reference D5650, may be used. It should be noted that these beads do not require any special treatment before use, which also constitutes a substantial advantage of the invention.

According to another advantageous characteristic of the process according to the invention, the factor VII activation step, preferably with dextran sulfate, is carried out in the cold at a controlled temperature advantageously of between 0° C. and +4° C., which makes it possible to ensure a very good activation of the factor VII to factor VIIa.

According to another advantageous characteristic of the process according to the invention, the above-mentioned activation step is followed by anion exchange chromatography of the DEAE type on the cryoprecipitate-free plasma containing the activated factor VII and also non-activated factor VII, so as selectively to adsorb essentially all the vitamin K-dependent factors, i.e. mainly activated factor VII, non-activated factor VII, factor IX, factor X and factor II. Thus the object of this selective adsorption is to remove a significant part of the undesirable proteins such as albumin.

According to yet another advantageous characteristic of the process according to the invention, non-selective desorption of all the vitamin K-dependent factors adsorbed on the above-mentioned DEAE ion exchange column is carried out. This can be done by eluting with any eluting buffer solution well known to those skilled in the art for carrying out this desorption on this type of gel.

Then the eluate obtained, containing all the vitamin K-dependent factors, is again passed over a specific anion exchange column of the quaternary amine type, preferably of the Q SEPHAROSE FAST FLOW ® resin type from PHARMACIA, which is in the form of beads of agarose crosslinked to the extent of about 6% and preferably comprising a small $C_1$–$C_6$ spacer arm, so as selectively to adsorb all the vitamin K-dependent factors.

This adsorption of the vitamin K-dependent factors in a specific manner on this column thus makes it possible to remove other contaminating proteins such as $\alpha$-antitrypsin and ceruloplasmin.

This selective adsorption on a column of the quaternary amine type constitutes a patentable characteristic of the process, which is independent of the factor VII activation. The same applies to the selective desorption mentioned below. The selective adsorption solution is preferably the buffer solution NaCl 150 mM, trisodium citrate 4 mM, pH 6.

The next stage is selective desorption of the activated factor VII and the non-activated factor VII by elution of the column with a so-called selective desorption buffer solution of the following composition:

| | |
|---|---|
| NaCl | 250 mM |
| trisodium citrate | 4 mM |
| pH 6 | |

The eluate obtained, which contains essentially activated factor VII and non-activated factor VII in aqueous form and is essentially free of the other vitamin K-dependent factors, then undergoes a viral inactivation step in known manner, for example by using a TNBP/Tween mixture in which the proportions of TNBP and Tween are respectively 0.3% and 1% relative to the total concentration of the solution of activated factor VII/factor VII, preferably for 6 h at 24° C., with agitation, in accordance with the process described in the document EP-A-0 131 740 or U.S. Pat. No. 4,540,573.

After inactivation, it is necessary to remove the residual mixture of TNBP/Tween inactivators and adsorption is carried out again on the same column of Q SEPHAROSE FAST FLOW ® resin, mentioned above, with a buffer solution which permits selective adsorption, namely NaCl 150 mM, trisodium citrate 4 mM, pH 6.

This adsorption is then followed by desorption with the same desorption solution (NaCl 250 mM, trisodium citrate 4 mM, pH 6) to give an eluate containing the high-purity activated factor VII and the non-activated factor VII and essentially free of vitamin K-dependent factors as well as factors VIIIC and VIIICAg.

This eluate can then also be subjected to diafiltration against a buffer which is preferably compatible with injection in humans (such as the buffer NaCl 100 mM, trisodium citrate 4 mM, lysine 3 g/l, pH 7); the product of diafiltration can advantageously be concentrated to 5000 IU of activated factor VII per 20 ml bottle and can be filtered under sterile conditions on a sterilizing filter with a pore size of 0.2 micrometer, and then lyophilized if desired.

It should be noted that the process according to the invention makes it possible to obtain not only a factor VII of high purity, but also a very high degree of activation of the factor VII.

Consequently the expression "high-purity activated factor VII", in the description and in the claims, means that the factor VIIa/factor VII ratio is greater than 5, preferably greater than 7 and particularly preferably of the order of 10, while the specific activity of the activated factor VII is greater than 200 IU/mg of protein.

The thrombogenic activity is negative after 6 h at 37° C. according to the free thrombin test.

The invention also covers the high-purity activated factor VII obtained by the process described above.

Further objects, characteristics and advantages of the invention will become clearly apparent from the following explanatory description referring to two Examples of manufacture, which are given simply by way of illustration and cannot in any way limit the scope of the invention. In the Examples, all the percentages are given by weight, unless indicated otherwise.

EXAMPLE 1

5 l of cryoprecipitate-free plasma kept at 4° C. are adjusted to an ionic strength of <140 mM in respect of NaCl.

0.1 g of dextran sulfate beads (Sigma D5650) per liter of plasma is added batchwise. After agitation for 1 h at 4° C., the mixture is decanted and the supernatant is recovered and incubated for 90 min with 0.5 g/l of DEAE-Sephadex A50 ®. After decantation, the gel to which all the vitamin K-dependent factors have bound is washed with 1 l of the buffer trisodium citrate 4 mM, NaCl 140 mM, pH 7, making it possible to remove inter alia the albumin. The vitamin K-dependent factors are then eluted with this same buffer, the ionic strength of which has been increased to 500 mM in respect of NaCl. 500 ml of an eluate I are recovered.

This eluate I is subjected to diafiltration and concentrated to 250 ml using a cassette with a cut-off threshold of 10 Kd against the buffer trisodium citrate 4 mM, NaCl 150 mM, pH 6.

This solution is chromatographed on a column of diameter 9 cm containing 300 ml of Q SEPHAROSE FAST FLOW ® resin gel (Pharmacia), equilibrated with the same buffer. 5 l of this buffer will enable the α-antitrypsin and the ceruloplasmin to be removed. The factors VII/VIIa will be specifically desorbed by increasing the ionic strength to 250 mM in respect of NaCl. About 2 l of an eluate II are recovered.

Eluate II is then subjected to a viral inactivation step with a TNBP/Tween mixture which is such that the final concentration in the solution of factors VII/VIIa is 0.3% of TNBP and 1% of Tween, for 6 h at 24° C., with agitation.

After inactivation, the solution is subjected to diafiltration and concentrated to 250 ml against the buffer used for equilibrating the above-mentioned column of Q SEPHAROSE FAST FLOW ® resin (trisodium citrate 4 mM, NaCl 150 mM, pH 6). The solution is chromatographed again on Q SEPHAROSE FLOW ® resin with 2 l of a washing solution identical to the equilibration buffer, which makes it possible to remove the mixture of inactivators by making it pass into the non-retained fraction. With the buffer trisodium citrate 4 mM, NaCl 250 mM, pH 6, the factors VII/VIIa are selectively eluted relative to the other vitamin K-dependent factors to give an eluate III. This eluate of 2 l is then subjected to diafiltration against a buffer compatible with injection in humans (trisodium citrate 4 mM, NaCl 100 mM, lysine 3 g/l, pH 7), concentrated to 5000 IU of factor VIIa per 20 ml bottle and then lyophilized.

The results obtained by the process according to the invention on the pilot scale in 4 experiments each performed on 5 l of cryoprecipitate-free plasma, and, by way of comparison, on a so-called control batch by the same process but with omission of the dextran sulfate activation step, are reported in Table I.

The results are expressed in international units in Table I. The determinations are carried out at various stages of the process, as can easily be understood by those skilled in the art from a consideration of Table I.

TABLE I

|  | VII | VIIa | VIIa/VII | Yield VII % | Yield VIIa % | Control batch |||
|---|---|---|---|---|---|---|---|---|
|  |  |  |  |  |  | VII | VIIa | VIIa/VII |
| CFP* | 4212 ±318 | 7400 ±1030 | 1.7 ±0.3 | 100 | 100 | 3250 | 5000 | 2 |
| AFTER DEXTRAN SULFATE | 5415 ±616 | 35275 ±3985 | 6.9 ±1.3 | 127 ±10 | 500 ±81 |  |  |  |
| AFTER DEAE | 4292 ±253 | 54167 ±9610 | 13 ±2.8 | 99 ±9 | 657 ±93 | 1850 | 3600 | 2 |
| AFTER Q1 | 1960 ±390 | 26313 ±3870 | 15.8 ±3.3 | 44.7 ±6.4 | 359 ±31 | 1050 | 2030 | 2 |
| AFTER Q2 + LYO | 1500 ±244 | 17062 ±4320 | 11.7 ±2 | 33 ±4.5 | 234 ±54 | 940 | 1800 | 2 |

*CFP = cryoprecipitate-free plasma
Q1: 1st adsorption chromatography on Q Sepharose Fast Flow
Q2: 2nd adsorption chromatography on Q Sepharose Fast Flow
LYO: lyophilization Biological characteristics of the factor VIIa concentrate after reconstitution with 20 ml of distilled water:
VIIa: 172±277 IU/ml
VII: 14.3±1.4 IU/ml
VIIAg: 0.88±0.22 IU/ml
VIIa/VII: 12±2.5
Protein content: 0.82±0.07
AS VIIa: 208±36
AS VII: 17.5±1.6
II/IIa: <0.1 IU/ml
IX/IXa: <0.1 IU/ml
X/Xa: <0.1 IU/ml
VIIIC: <0.1 IU/ml
VIIICAg: <0.1 IU/ml The clotting factors are assayed by chronometric measurements on the shortening of the clotting time of a deficient plasma for a missing factor. This factor will be provided by the sample.

The degree of activation of factor VII is determined by using human thromboplastin and bovine thromboplastin according to the method described by Van Deijk et al., Haemostasis, 13, 1983.

Activated factor VII has a greater affinity than factor VII for bovine thromboplastin, whereas they have the same affinity for human thromboplastin. The degree of activation is expressed by the ratio factor VII with bovine thromboplastin
factor VII with human thromboplastin The reference value of this ratio is 1 in a normal human plasma.

EXAMPLE 2

Results obtained on an industrial batch of 300 l of plasma

The procedure is as described in Example 1 except that the initial amount of plasma used is 300 l.

The results obtained are expressed in Table II below.

TABLE II

|  | VIIa | VII | AS VIIa | AS VII |
|---|---|---|---|---|
| CFP | 391300 | 301154 | 0.034 | 0.022 |
| AFTER DEXTRAN SULFATE | 2530000 | 361507 | 0.24 | 0.029 |
| AFTER DEAE | 1282500 | 157800 | 8.3 | 1.02 |
| AFTER Q1 | 1399650 | 150500 | 73 | 7.8 |
| AFTER Q2 + LYO | 965000 | 98800 | 244 | 32.5 |

CFP, Q1, Q2 and LYO: see Table I for meanings

Biological characteristics of the factor VIIa concentrate after reconstitution with 20 ml of distilled water:
VIIa: 244 IU/ml
VII: 32.5 IU/ml
VIIa/VII: 7.5
Protein content: 1 g/l
AS VIIa: 244
AS VII: 32.5
II/IIa: <0.1 IU/ml
IX/IXa: <0.1 IU/ml
X/Xa: <0.1 IU/ml
VIIIC: <0.1 IU/ml
VIIICAg: <0.1 IU/ml It can thus be observed from the above Examples and the Tables expressing the results that with the control batch, without initial activation, the VII/VIIa ratio remains essentially unmodified, being close to the initial ratio of 1.5 for a normal plasma.

Furthermore, in addition to the fact that a very good activation ratio is obtained, the invention makes it possible to obtain an excellent degree of purification of factor VII by means of an extremely simple process which is easy to carry out, with a very good reproducibility.

Also, the product according to the invention has a very low thrombogenic activity. In fact, the free thrombin test (European PHARMACOPEIA 2nd edition, 554) is negative after 6 h at 37° C. with the product of the invention, which constitutes a preferred essential characteristic of the product of the invention, distinguishing it from the products of the prior art. The activated factor VII concentrates obtained by other processes, and the activated prothrombin concentrates of the prior art, such as, for example, FEIBA® or AUTOPLEX®, actually have a positive thrombogenic activity before 6 h.

It should also be noted that the activated factor VII concentrate according to the invention is not treated with antithrombin III on account of its purity, and therefore carries no risk of premature clotting.

Furthermore, especially with a view to lyophilization, the purity of the activated factor VII concentrate according to the present invention is such that said concentrate only requires the use of lysine for its stabilization, whereas the products of the prior art required the use of albumin for lyophilization; this reduces the cost and avoids injecting a protein of no use to the patient.

What is claimed is:

1. A process for the manufacture of a high purity concentrate containing activated factor VIIa, comprising:
   a) providing a plasma containing factor VII and free of cyroprecipitate;
   b) directly activating the factor VII in the plasma without the addition of exogenous proteins and without the precipitation of lipoproteins, to obtain a plasma free of cryoprecipitate containing an increased amount of activated factor VIIa, said activating comprising contacting said plasma with an amount of pulverulent dextran sulfate, insoluble in said plasma, sufficient to activate said factor VII without precipitation of lipoproteins; and
   c) purifying said plasma containing activated factor VIIa and non-activated factor VII by chromatography with an ion exchange resin.

2. A process for the manufacture of a high purity concentrate containing activated factor VIIa, comprising:
   a) providing a plasma containing factor VII and free of cryoprecipitate;
   b) directly activating the factor VII in the plasma without the addition of exogenous proteins and without the precipitation of lipoproteins, to obtain a plasma free of cryoprecipitate containing an increased amount of activated factor VIIa, said activating comprising contacting said plasma with pulverulent dextran sulfate, insoluble in said plasma, in an amount of about 0.1 g per liter of plasma; and
   c) purifying said plasma containing activated factor VIIa and non-activated factor VII by chromatography with an ion exchange resin.

3. A process according to claim 1 or 2 wherein the dextran sulfate is in the form of beads.

4. A process according to claims 1 or 2 wherein the direct activation of factor VII is carried out at a temperature of between about 0° C. and about +4° C.

5. A process according to one of claims 1 or 2 wherein the direct activation is followed by anion exchange chromatography with a DEAE anion exchange resin on the cryoprecipitate-free plasma containing the activated factor VIIa and non-activated factor VII, so as selectively to adsorb all vitamin K-dependent factors, including activated factor VII and non-activated factor VII, present in the plasma.

6. A process according to claim 5 wherein the vitamin K-dependent factors adsorbed on the DEAE ion exchange column are non-selectively desorbed into a first eluate.

7. A process according to claim 6 wherein the first eluate containing the vitamin K-dependent factors, is passed over an anion exchange resin of the quaternary amine type, so as selectively to adsorb vitamin K-dependent factors present in the first eluate.

8. A process according to claim 5, wherein said anion exchange resin of the quaternary amine type is in the form of agarose crosslinked to the extent of about 6%.

9. A process according to claim 8, wherein the crosslinked agarose comprises a small $C_1$–$C_6$ spacer arm bearing said quaternary amine.

10. A process according to claim 7 additionally comprising selective desorption of the activated factor VIIa and the non-activated factor VII by elution of the quaternary amine resin with a selective desorption buffer solution into a second eluate.

11. A process according to claim 10 wherein the selective desorption buffer comprises 4 mM trisodium citrate and 250 mM sodium chloride, and has a pH of about 6.

12. A process according to claim 10 wherein the second eluate, which contains activated factor VIIa and non-activated factor VII in aqueous form and is substantially free of other vitamin K-dependent factors, is then subjected to a viral inactivation step.

13. A process according to claim 12, wherein the viral inactivation step comprises treating the selective desorption buffer eluate with a TNBP/Tween mixture comprising 0.3% TNBP with respect to the total factor VII present and 1% Tween with respect to the total factor VII present, passing the treated eluate over a quaternary amine column with a buffer permitting selective adsorption, and selectively desorbing the factor VII from the column with a selective desorption buffer.

14. A process according to claim 13, wherein the selective adsorption buffer comprises 150 mM NaCl and 4 mM sodium citrate, and has a pH of about 6.

15. A process according to claim 12 wherein the virally inactivated second eluate is subjected to diafiltration against a second buffer to form a diafiltration product.

16. A process according to claim 15, wherein the second buffer is compatible with injection in humans, comprises 100 mM NaCl and 4 mM trisodium citrate, and has a pH of about 7.

17. A process according to claim 16, wherein said second buffer also comprises 3 g/l lysine.

18. A process according to claim 15 wherein the product of diafiltration is concentrated to 5000 IU of activated factor VIIIa per 20 ml and filtered under sterile conditions on a sterilizing filter with a pore size of 0.2 micrometer.

19. A process according to claim 18, additionally comprising lyophilizing the filtered product.

20. A process according to claim 1 or 2, wherein the concentrate has a factor VIIa/factor VII ratio greater than 5.

21. A process according to claim 20, wherein said ratio is greater than 7.

22. A process according to claim 21, wherein said ratio is about 10.

23. A process according to claim 1 or 2, wherein the plasma is of human origin.

* * * * *